(12) United States Patent
Shikii et al.

(10) Patent No.: US 11,478,605 B2
(45) Date of Patent: Oct. 25, 2022

(54) AUTONOMIC NERVE CONTROL DEVICE, AUTONOMIC NERVE CONTROL SYSTEM, AND AUTONOMIC NERVE CONTROL METHOD

(71) Applicant: Panasonic Intellectual Property Management Co., Ltd., Osaka (JP)

(72) Inventors: Shinichi Shikii, Nara (JP); Koichi Kusukame, Nara (JP); Kenichiro Nosaka, Osaka (JP); Aki Yoneda, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 273 days.

(21) Appl. No.: 16/637,163

(22) PCT Filed: Sep. 26, 2018

(86) PCT No.: PCT/JP2018/035754
§ 371 (c)(1),
(2) Date: Feb. 6, 2020

(87) PCT Pub. No.: WO2019/065765
PCT Pub. Date: Apr. 4, 2019

(65) Prior Publication Data
US 2020/0368490 A1      Nov. 26, 2020

Related U.S. Application Data

(60) Provisional application No. 62/564,714, filed on Sep. 28, 2017.

(51) Int. Cl.
*A61M 21/02* (2006.01)
*A61B 5/0205* (2006.01)
(Continued)

(52) U.S. Cl.
CPC ......... *A61M 21/02* (2013.01); *A61B 5/02055* (2013.01); *A61B 5/18* (2013.01);
(Continued)

(58) Field of Classification Search
CPC ............ A61B 2503/22; A61B 5/02055; A61B 5/0245; A61B 5/18; A61B 5/352;
(Continued)

(56) References Cited

U.S. PATENT DOCUMENTS

| 7,711,415 B1* | 5/2010 | Farazi ................... A61B 5/349 600/509 |
| 2003/0149344 A1* | 8/2003 | Nizan ..................... G06F 3/011 600/300 |

(Continued)

FOREIGN PATENT DOCUMENTS

| JP | 5-103837 | 4/1993 |
| JP | 2002-89927 | 3/2002 |

(Continued)

OTHER PUBLICATIONS

International Search Report (ISR) dated Dec. 4, 2018 in International (PCT) Application No. PCT/JP2018/035754.

*Primary Examiner* — Thaddeus B Cox
*Assistant Examiner* — Marc D. Honrath
(74) *Attorney, Agent, or Firm* — Wenderoth, Lind & Ponack, L.L.P.

(57) ABSTRACT

An autonomic nerve control device includes an obtainer that obtains a physiological quantity of a user before the user occupies a moving body, and a controller that controls the autonomic nerves of the user occupying the moving body based on the physiological quantity of the user obtained by the obtainer.

10 Claims, 7 Drawing Sheets

(51) Int. Cl.
*A61B 5/18* (2006.01)
*B60H 1/00* (2006.01)
*G06F 3/16* (2006.01)
*A61B 5/0245* (2006.01)
*A61M 21/00* (2006.01)

(52) U.S. Cl.
CPC ......... *B60H 1/00742* (2013.01); *G06F 3/165* (2013.01); *A61B 5/0245* (2013.01); *A61M 2021/0027* (2013.01); *A61M 2021/0066* (2013.01); *A61M 2021/0088* (2013.01); *A61M 2205/3303* (2013.01); *A61M 2205/3368* (2013.01); *A61M 2205/36* (2013.01); *A61M 2210/04* (2013.01); *A61M 2230/04* (2013.01); *A61M 2230/50* (2013.01)

(58) Field of Classification Search
CPC ....... A61B 5/486; A61B 5/681; A61B 5/7405; A61B 5/742; A61B 5/746; A61M 2021/0016; A61M 2021/0022; A61M 2021/0027; A61M 2021/0044; A61M 2021/0066; A61M 2021/0088; A61M 21/00; A61M 21/02; A61M 2205/3303; A61M 2205/3368; A61M 2205/3375; A61M 2205/3553; A61M 2205/3561; A61M 2205/3592; A61M 2205/36; A61M 2205/502; A61M 2205/505; A61M 2205/52; A61M 2205/581; A61M 2205/583; A61M 2210/04; A61M 2230/04; A61M 2230/50; B60H 1/00742; G06F 3/165; G06F 3/167
See application file for complete search history.

(56) References Cited

U.S. PATENT DOCUMENTS

| | | | |
|---|---|---|---|
| 2004/0230252 A1* | 11/2004 | Kullok | A61M 21/00 607/48 |
| 2017/0011210 A1* | 1/2017 | Cheong | A61B 5/681 |

FOREIGN PATENT DOCUMENTS

| | | | | | |
|---|---|---|---|---|---|
| JP | 2006102362 | A | * | 4/2006 | |
| JP | 2008-125802 | | | 6/2008 | |
| JP | 2010-75312 | | | 4/2010 | |
| JP | 2010-104455 | | | 5/2010 | |
| JP | 2010099410 | A | * | 5/2010 | |
| JP | 2017012730 | A | * | 1/2017 | .......... A61B 5/0077 |
| KR | 20100118879 | A | * | 11/2010 | |
| WO | WO-2005006973 | A1 | * | 1/2005 | ............... A61B 5/18 |

* cited by examiner

AUTONOMIC NERVE CONTROL DEVICE, AUTONOMIC NERVE CONTROL SYSTEM, AND AUTONOMIC NERVE CONTROL METHOD

TECHNICAL FIELD

The present disclosure relates to an autonomic nerve control device, an autonomic nerve control system, and an autonomic nerve control method for controlling a user's autonomic nerves.

BACKGROUND ART

There is a conventional device that creates a favorable biological state for a user by controlling the biological state of the user (see PTL 1, for example).

PTL 1 discloses a technique in which a user's biological information, i.e., a physiological quantity, is measured, the user's biological state is estimated based on the measured physiological quantity, and a signal for stimulating the user is then issued based on the user's estimated biological state in order to put the user's biological state into a desired biological state.

CITATION LIST

Patent Literature

PTL 1: Japanese Unexamined Patent Application Publication No. H5-103837

SUMMARY OF THE INVENTION

Technical Problem

In a moving body such as a vehicle or the like, it is conceivable to control the biological state, and specifically the autonomic nerves, of a user occupying the moving body. In this case, there is a problem in that if a physiological quantity of the user is detected within the moving body and the user's autonomic nerves are controlled in accordance with the detection result, vibrations and the like in the moving body will disrupt the user's autonomic nerves, making it impossible to appropriately detect the user's physiological quantity and, by extension, impossible to appropriately control the user's autonomic nerves.

The present disclosure provides an autonomic nerve control device and the like capable of appropriately controlling the autonomic nerves of a user occupying a moving body.

Solutions to Problem

To solve the aforementioned problem, an autonomic nerve control device according to one aspect of the present disclosure includes: an obtainer that obtains a physiological quantity of a user before the user occupies a moving body; and a controller that controls autonomic nerves of the user occupying the moving body based on the physiological quantity of the user obtained by the obtainer.

Additionally, an autonomic nerve control system according to one aspect of the present disclosure includes: the above-described autonomic nerve control device; a detecting device that is disposed outside the moving body and that detects the physiological quantity of the user; and an output device that is disposed in the moving body and that is driven by the controller to control the autonomic nerves of the user occupying the moving body.

Additionally, an autonomic nerve control method according to one aspect of the present disclosure includes: obtaining a physiological quantity of a user before the user occupies a moving body; and controlling autonomic nerves of the user occupying the moving body based on the physiological quantity of the user obtained in the obtaining step.

Advantageous Effect of Invention

The autonomic nerve control device and the like according to an aspect of the present disclosure are capable of appropriately controlling the autonomic nerves of a user occupying a moving body.

DESCRIPTION OF EXEMPLARY EMBODIMENT

Overview of Present Disclosure

Figure 1:
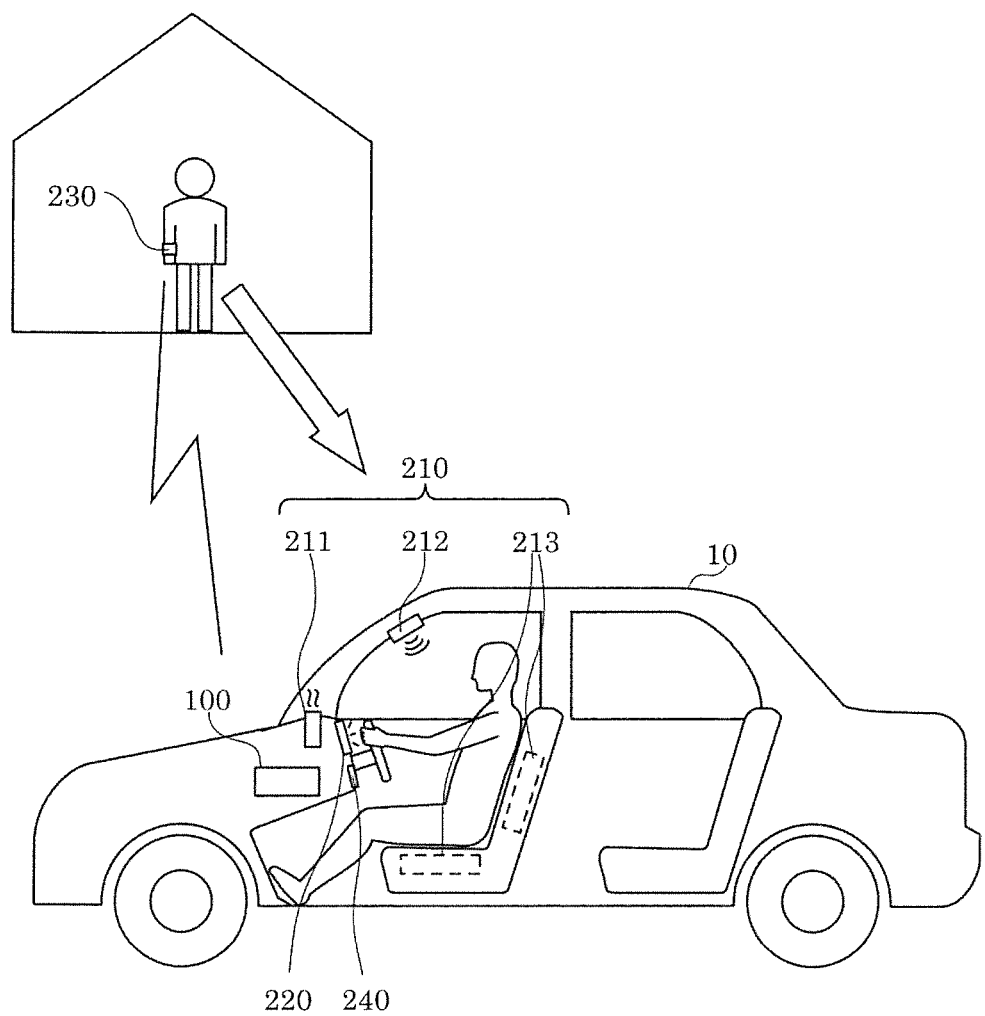
FIG. 1 is a schematic diagram illustrating an overview of an overall system including an autonomic nerve control device according to an embodiment.

To solve the aforementioned problem, an autonomic nerve control device according to one aspect of the present disclosure includes: an obtainer that obtains a physiological quantity of a user before the user occupies a moving body; and a controller that controls autonomic nerves of the user occupying the moving body based on the physiological quantity of the user obtained by the obtainer.

Through this, the user's physiological quantity is obtained before the user occupies the moving body, and thus the user's physiological quantity is obtained in a state where the physiological quantity is not being affected by vibrations or the like caused by movement in the moving body. Additionally, the autonomic nerves of the user occupying the moving body are controlled based on the user's physiological quantity that has been obtained, and thus when a given user among a plurality of users occupies the moving body, favorable autonomic nerve control is executed for the user occupying the moving body. As such, the autonomic nerves of the user occupying the moving body can be controlled appropriately.

For example, the autonomic nerve control device according to one aspect of the present disclosure further includes a calculator that calculates an activation time ratio, expressing a ratio of an activation time of parasympathetic nerves of the user to an activation time of sympathetic nerves of the user, from the physiological quantity of the user obtained by the obtainer. Here, the controller carries out control for activating the sympathetic nerves of the user when the activation time ratio calculated by the calculator is greater than or equal to a predetermined ratio, and carries out control for activating the parasympathetic nerves of the user when the activation time ratio calculated by the calculator is less than the predetermined ratio.

Through this, the sympathetic nerves or parasympathetic nerves of the user occupying the moving body are controlled using the activation time ratio between the sympathetic nerves and the parasympathetic nerves of the user before the user occupies the moving body. As such, the sympathetic nerves or the parasympathetic nerves of the autonomic nerves of the user occupying the moving body can be controlled more appropriately.

Additionally, for example, the obtainer obtains a holiday physiological quantity of the user, and the calculator calculates a holiday activation time ratio of the user from the holiday physiological quantity of the user obtained by the obtainer, and calculates the predetermined ratio based on the calculated holiday activation time ratio of the user.

Through this, the activation time ratio during which the user's autonomic nerves are most stable, i.e., the activation time ratio of the autonomic nerves while on a holiday considered appropriate by the user, serves as a reference for the determination in the control carried out by the controller. As such, the user occupying the moving body can be controlled to an autonomic nerve state that is more favorable for that user.

Additionally, for example, the obtainer obtains an R-R interval, calculated from a heartbeat waveform of the user, as the physiological quantity of the user, and the calculator: calculates an LF/HF value from the R-R interval obtained by the obtainer; and calculates the activation time ratio by determining a time for which the calculated LF/HF value is greater than or equal to a predetermined LF/HF value to be an activation time of the sympathetic nerves, and determining a time for which the calculated LF/HF value is less than the predetermined LF/HF value to be an activation time of the parasympathetic nerves.

Through this, the activation time ratio can be calculated easily, without using complex information, simply by detecting the user's electrocardiographic waveform as the user's physiological quantity. Thus according to the autonomic nerve control device, the user's autonomic nerves can be controlled appropriately using a simpler configuration.

Additionally, for example, the obtainer obtains a peripheral skin temperature of the user as the physiological quantity of the user, and the calculator: calculates the activation time ratio by determining a time for which the peripheral skin temperature obtained by the obtainer is less than a predetermined skin temperature to be an activation time of the sympathetic nerves, and determining a time for which the peripheral skin temperature is greater than or equal to the predetermined skin temperature to be an activation time of the parasympathetic nerves.

Through this, the activation time ratio can be calculated easily, without using complex information, simply by detecting the peripheral skin temperature at a fingertip, the tip of the nose, or the like of the user as the user's physiological quantity. Thus according to the autonomic nerve control device, the user's autonomic nerves can be controlled appropriately using a simpler configuration.

Additionally, for example, the controller controls the autonomic nerves of the user by controlling a breathing control device that controls breathing of the user.

Through this, for example, the depth, rhythm, and the like of the user's breathing can be controlled by controlling a device commonly provided in a moving body, such as an audio device or the like, to output audio guidance for communicating a breathing rhythm. According to such a configuration, the user's autonomic nerves can be controlled appropriately using a simpler configuration. Additionally, the depth, rhythm, and so on of the user's breathing can be controlled by controlling an expanding/contracting device that is disposed in a seat of the moving body and that is capable of expanding and contracting, for example. According to such a configuration, even when the user is using the audio device to listen to music or the like, the user's breathing can be controlled without using the audio device.

Additionally, for example, the controller controls the autonomic nerves of the user by controlling at least one of an audio device and an air conditioning device.

Through this, the user's autonomic nerves are controlled simply by controlling a device commonly provided in a moving body, such as an audio device, an air conditioning device, or the like. Thus according to the autonomic nerve control device, the user's autonomic nerves can be controlled appropriately using a simpler configuration.

Additionally, for example, the controller further causes a presenting device to present the physiological quantity of the user and details of control being executed for controlling the autonomic nerves of the user.

Through this, the user can correctly understand his or her own biological state and the details of the control. Thus even when, for example, a device in the moving body has automatically begun operating to control the user's autonomic nerves, the user's autonomic nerves can be controlled appropriately without the user mistakenly stopping the device in the moving body.

Additionally, for example, the obtainer further obtains destination information indicating a destination of the moving body; and when control for activating the parasympathetic nerves of the user is carried out, the controller calculates a route to the destination that is not a shortest route based on the destination information, and causes a presenting device to present a result of the calculation.

Through this, the user can be prompted to extend the time for which he or she occupies the moving body. This makes it easier to activate the user's parasympathetic nerves within the moving body. In other words, the user can become more relaxed in the moving body.

Additionally, for example, when control is carried out for activating the sympathetic nerves of the user, the controller causes a presenting device to present recommendation information recommending that the user walk.

Through this, the activation of the sympathetic nerves can be prompted by having the user walk to his or her destination. This makes it possible to appropriately activate the user's sympathetic nerves after the user has exited the moving body.

Additionally, for example, the autonomic nerve control device according to one aspect of the present disclosure further includes a storage unit that stores the physiological quantity of the user, and when occupancy information indicating that the user has entered the moving body is obtained, the obtainer obtains the physiological quantity of the user from the storage unit.

Through this, the control of the user's autonomic nerves can be started automatically at the timing at which the user occupies the moving body. As such, the control of the user's autonomic nerves can be started at an appropriate timing when the user is occupying the moving body.

Additionally, an autonomic nerve control system according to one aspect of the present disclosure includes: the above-described autonomic nerve control device; a detecting device that is disposed outside the moving body and that detects the physiological quantity of the user; and an output device that is disposed in the moving body and that is driven by the controller to control the autonomic nerves of the user occupying the moving body.

Through this, the same effects as those of the above-described autonomic nerve control device can be achieved.

Additionally, an autonomic nerve control method according to one aspect of the present disclosure includes: obtaining a physiological quantity of a user before the user occupies a moving body; and controlling autonomic nerves of the user occupying the moving body based on the physiological quantity of the user obtained in the obtaining step.

Through this, the user's physiological quantity is obtained before the user occupies the moving body, and thus the user's physiological quantity can be obtained in a state where the physiological quantity is not being affected by vibrations or the like caused by movement in the moving body. Additionally, the autonomic nerves of the user occupying the moving body are controlled based on the user's physiological quantity that has been obtained, and thus when a given user among a plurality of users occupies the moving body, favorable autonomic nerve control can be executed for the user occupying the moving body. Thus with the autonomic nerve control method according to one aspect of the present disclosure, the autonomic nerves of a user occupying a moving body can be controlled appropriately.

Embodiments of the present disclosure will be described hereinafter with reference to the drawings. Note that the following embodiments describe comprehensive or specific examples of the present disclosure. As such, the numerical values, constituent elements, and positioning and connection configurations of the constituent elements, as well as the processes (steps), orders of the steps, and the like, are merely examples, and are not intended to limit the present disclosure. Thus, of the constituent elements in the following embodiments, constituent elements not denoted in the independent claims, which express the broadest interpretation of the present disclosure, will be described as optional constituent elements.

The drawings are schematic diagrams, and are not necessarily exact illustrations. As such, the scales and so on are not necessarily consistent from drawing to drawing. Configurations that are substantially the same are given the same reference signs in the drawings, and redundant descriptions may be omitted or simplified.

The following descriptions may contain the phrase "greater than or equal to", as in "greater than or equal to a predetermined ratio", but this phrase is not used in a strict sense. For example, "greater than or equal to a predetermined ratio" may mean greater than the predetermined ratio. Furthermore, "greater than or equal to a predetermined ratio" being contrasted with "less than a predetermined ratio" indicates a distinction made using the predetermined ratio as a boundary, and the phrases may therefore mean "greater than a predetermined ratio" and "less than or equal to a predetermined ratio", respectively.

Embodiment

Configuration

First, the configuration of autonomic nerve control device 100 according to an embodiment will be described with reference to FIGS. 1 and 2.

Figure 2:
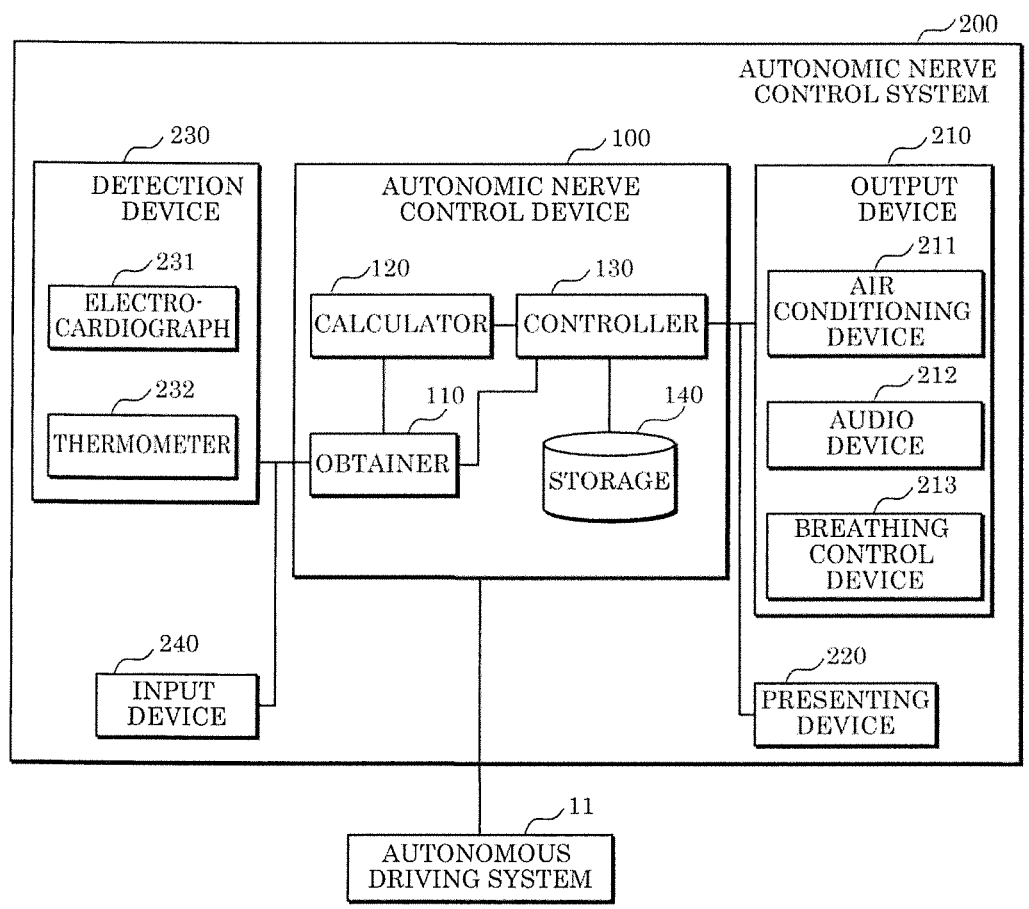
FIG. 2 is a block diagram illustrating a characteristic functional configuration of the autonomic nerve control device according to the embodiment.

FIG. 1 is a schematic diagram illustrating an overview of an overall system including autonomic nerve control device 100 according to an embodiment. Note that FIG. 1 illustrates a case where the constituent elements of autonomic nerve control device 100 are arranged within moving body 10 as an example. Autonomic nerve control device 100 may be communicatively connected to output device 210, detection device 230, and the like, and may be arranged in a user's home, office, or the like, for example. FIG. 2 is a block diagram illustrating a characteristic functional configuration of autonomic nerve control device 100 according to the embodiment.

Autonomic nerve control device 100 is a device, arranged within moving body 10 or the like, for controlling the autonomic nerves of a user occupying (riding in) moving body 10 based on a physiological quantity of the user detected outside moving body 10. The user detects his or her own physiological quantity using detection device 230, such as electrocardiograph 231, thermometer 232, or the like, for example. Autonomic nerve control device 100 is communicatively connected to detection device 230, for example, over a wire or wirelessly, and obtains the physiological quantity detected by the user using detection device 230. Based on the obtained physiological quantity of the user, autonomic nerve control device 100 controls the user's autonomic nerves by controlling moving body 10, and specifically by controlling output device 210, such as air conditioning device 211, audio device 212, breathing control device 213, and the like, arranged within moving body 10.

Moving body 10 is a vehicle such as an automobile, a motorcycle, a bicycle, or the like. In the present embodiment, moving body 10 is an automobile capable of autonomous driving.

Autonomic nerve control device 100 includes obtainer 110, calculator 120, controller 130, and storage 140.

Obtainer 110 obtains the physiological quantity of the user subject to autonomic nerve control from detection device 230. Specifically, obtainer 110 includes an interface connected to detection device 230 by a wire or wirelessly, obtains the user's physiological quantity detected by detection device 230, and outputs the obtained physiological quantity of the user to controller 130.

Calculator 120 calculates an activation time ratio, expressing the ratio of an activation time of the user's parasympathetic nerves to an activation time of the user's sympathetic nerves, from the user's physiological quantity obtained by obtainer 110.

Controller 130 carries out control for activating the user's sympathetic nerves when the activation time ratio calculated by calculator 120 is greater than or equal to a predetermined ratio. Controller 130 also carries out control for activating the user's parasympathetic nerves when the activation time ratio calculated by calculator 120 is less than the predetermined ratio. The predetermined ratio may be determined in advance as desired. Additionally, the predetermined ratio may be determined from the user's holiday activation time ratio.

For example, obtainer 110 obtains the user's holiday physiological quantity. Calculator 120 calculates the user's holiday activation time ratio from the user's holiday physiological quantity obtained by obtainer 110, and then calculates the predetermined ratio based on the user's holiday activation time ratio which has been calculated. For example, calculator 120 takes the user's holiday activation time ratio, which has been calculated, as the predetermined ratio.

Obtainer 110 obtains an R-R interval, calculated from the user's heartbeat waveform (electrocardiographic waveform), as the user's physiological quantity, for example. In this case, calculator 120 calculates an LF/HF value from the R-R interval obtained by obtainer 110. Calculator 120 calculates the activation time ratio by determining a time for which the calculated LF/HF value is greater than or equal to a predetermined LF/HF value to be the sympathetic nerve activation time, and determining a time for which the calculated LF/HF value is less than the predetermined LF/HF value to be the parasympathetic nerve activation time.

The R-R interval is a time interval between two adjacent R waves in an electrocardiographic waveform. In a typical electrocardiographic waveform, a P wave, a Q wave, an R wave, an S wave, a T wave, and a U wave appear in synchronization with the movement in each beat of the heart. In the electrocardiographic waveform, the R wave has a high amplitude, and changes drastically per unit of time. The R wave is therefore used to detect a heartbeat. The specific method for detecting the R wave is not particularly limited. For example, the R wave can be detected by detecting a time corresponding to the maximum amplitude in a section where the amplitude is greater than or equal to a predetermined threshold as an R wave time. The time interval between a detected R wave time and the R wave time detected the previous time is the R-R interval. Electrocardiograph 231 detects the R-R interval from the user's electrocardiographic waveform that has been measured, for example. Obtainer 110 obtains the user's R-R interval detected by electrocardiograph 231.

The LF/HF value is the area of a frequency band on a low-frequency side (LF value) relative to the area of a frequency band on a high-frequency side (HF value), obtained by subjecting time changes in the R-R interval to a Fourier transform. For example, the LF value is a frequency band of 0.04 Hz to 0.15 Hz, and the HF value is a frequency band of 0.15 Hz to 0.4 Hz. Obtainer 110 obtains the R-R interval from electrocardiograph 231 every predetermined amount of time, for example. Calculator 120 calculates the LF/HF value by subjecting time changes in the R-R interval obtained by obtainer 110 to a Fourier transform.

Note that autonomic nerve control device 100 may include a timer such as an RTC (Real Time Clock) or the like for measuring the time.

Additionally, obtainer 110 may obtain time information from a device outside autonomic nerve control device 100, for example.

Additionally, obtainer 110 may obtain the user's electrocardiographic waveform detected by electrocardiograph 231 as the user's physiological quantity, and in this case, calculator 120 calculates the R-R interval based on the user's electrocardiographic waveform obtained by obtainer 110, for example.

Obtainer 110 also obtains the user's peripheral skin temperature as the user's physiological quantity, for example. In this case, calculator 120 calculates the activation time ratio by determining a time for which the peripheral skin temperature obtained by obtainer 110 is less than a predetermined skin temperature to be the sympathetic nerve activation time, and determining a time for which the peripheral skin temperature is greater than or equal to the predetermined skin temperature to be the parasympathetic nerve activation time.

The peripheral skin temperature is the temperature of the skin at any location on the human body relatively far from the trunk, such as a fingertip, the tip of the nose, or the like. Thermometer 232 detects the peripheral skin temperature at a fingertip, the tip of the nose, or the like as the user's physiological quantity.

When obtainer 110 obtains the activation time ratio calculated by calculator 120 as the user's physiological quantity, obtainer 110 sends the user's physiological quantity to controller 130 rather than to calculator 120. In this case, autonomic nerve control device 100 need not include calculator 120.

Controller 130 is a control device that controls output device 210 based on the user's physiological quantity obtained by obtainer 110 so as to control the user's autonomic nerves. Specifically, by controlling output device 210 based on the user's physiological quantity obtained by obtainer 110, controller 130 activates the user's sympathetic nerves or activates the user's parasympathetic nerves.

For example, controller 130 controls the user's autonomic nerves by controlling breathing control device 213, which controls the user's breathing. It is sufficient for breathing control device 213 to be capable of controlling the depth, rhythm, and so on of the user's breathing. Breathing control device 213 is an audio device, for example, and the depth, rhythm, and so on of the user's breathing is controlled by controller 130 causing breathing control device 213 to output audio guidance for communicating a breathing rhythm. Additionally, breathing control device 213 is an expanding/contracting device, disposed in a seat of moving body 10 and capable of expanding and contracting, for example, and the depth, rhythm, and so on of the user's breathing is controlled by controller 130 controlling breathing control device 213.

Additionally, controller 130 controls the user's autonomic nerves by controlling at least one of audio device 212 and air conditioning device 211, for example.

Additionally, controller 130 causes presenting device 220 to present the user's physiological quantity obtained by obtainer 110 and the details of control being executed for controlling the user's autonomic nerves, for example. Presenting device 220 is, for example, an audio device capable of outputting audio and/or a display device capable of displaying images, video, and the like.

Additionally, when control is carried out for activating the user's sympathetic nerves, controller 130 causes presenting device 220 to present recommendation information recommending that the user walk, for example.

Calculator 120 and controller 130 are realized by a CPU (Central Processing Unit) and storage 140 in which a control program executed by the CPU is stored, for example. ROM (Read Only Memory), RAM (Random Access Memory), an HDD (Hard Disk Drive), an SSD (Solid State Drive), or the like are examples of storage 140. Note that calculator 120 and controller 130 may include dedicated electronic circuits or the like in which the control program is implemented by hardware. Additionally, calculator 120 and controller 130 may be realized by individual CPUs, or by the same CPU.

Storage 140 stores a control program executed by calculator 120, controller 130, and the like.

Storage 140 also stores the user's physiological quantity, for example. Controller 130 causes the user's physiological quantity, obtained by obtainer 110, to be stored in storage 140, for example. Obtainer 110 obtains the user's physiological quantity from storage 140 when occupancy information, which indicates that the user is occupying moving body 10, has been obtained. Obtainer 110 may obtain the occupancy information from a human sensor (not shown) provided in moving body 10, i.e., information indicating that the user has been detected within moving body 10, for example. Additionally, obtainer 110 may obtain the occupancy information indicating that the user has occupied moving body 10 from input device 240, which accepts operations from the user, when input device 240 has accepted an input from the user, for example.

Storage 140 is memory such as ROM, RAM, or the like, for example.

Autonomic nerve control system 200 includes autonomic nerve control device 100, output device 210, presenting device 220, detection device 230, and input device 240.

Output device 210 is arranged in moving body 10, and is driven by controller 130 to control the autonomic nerves of the user occupying moving body 10. Specifically, output device 210 is a device that outputs a stimulus to the user's autonomic nerves. Output device 210 includes air conditioning device 211, audio device 212, and breathing control device 213, for example.

Air conditioning device 211 is an air conditioner that controls air conditioning in the user's surrounding environment. The states of operations such as air temperature, air speed, air direction, air amount, and the like in air conditioning device 211 are controlled by controller 130 included in autonomic nerve control device 100, and air conditioning device 211 activates the sympathetic nerves or parasympathetic nerves of the user's autonomic nerve by changing the temperature in the user's surrounding environment and/or blowing air at the user.

Audio device 212 is an audio device including an amplifier, a speaker, and the like for emitting sound. Controller 130 controls the user's autonomic nerve by selecting music, stored in storage 140 in advance, for activating the sympathetic nerves or activating the parasympathetic nerves, and causing audio device 212 to output the selected music, for example.

Breathing control device 213 is an audio device, for example, and the depth, rhythm, and so on of the user's breathing is controlled by controller 130 causing breathing control device 213 to output audio guidance for communicating a breathing rhythm. Additionally, breathing control device 213 is an expanding/contracting device, disposed in a seat of moving body 10 and capable of expanding and contracting, for example, and the depth, rhythm, and so on of the user's breathing is controlled by controller 130 controlling breathing control device 213. In the present embodiment, breathing control device 213 is an expanding/contracting device disposed in a seat of moving body 10 and capable of expanding and contracting.

Note that output device 210 may be any device capable of activating the sympathetic nerves or parasympathetic nerves of the user subject to autonomic nerve control, and may be an illumination device, an aroma generator, a humidifier, a dehumidifier, or the like, for example.

Presenting device 220 is a device for presenting information such as the user's physiological quantity to the user. Presenting device 220 is, for example, an audio device capable of outputting audio and/or a display device capable of displaying images, video, and the like.

Detection device 230 is a sensor, disposed outside moving body 10, that detects the user's physiological quantity. Detection device 230 includes electrocardiograph 231 and thermometer 232, for example.

Electrocardiograph 231 is a detection device that detects the user's electrocardiographic waveform as the user's physiological quantity. Note that by detecting the user's electrocardiographic waveform, electrocardiograph 231 may detect the user's R-R interval as the user's physiological quantity.

Thermometer 232 detects the user's body temperature. Specifically, thermometer 232 detects the user's peripheral skin temperature.

Note that it is sufficient for detection device 230 to be capable of detecting a physiological quantity of the user subject to autonomic nerve control. For example, detection device 230 may be a sensor that detects the user's physiological quantity by making contact with the user, or may be a device that detects the user's physiological quantity without making contact with the user, such as a thermal image capturing device including a thermal image sensor for capturing a thermal image, for example. The thermal image sensor is an image sensor that measures far infrared light, such as a bolometer, a thermopile meter, or the like, for example. Note that FIG. 1 schematically illustrates a wristband-type wearable electrocardiograph 231, which detects the user's physiological quantity by making contact with the user, as detection device 230.

Input device 240 is an interface such as a touch panel, a keyboard, or the like that accepts user operations.

Here, moving body 10 may be an autonomously-driven vehicle capable of autonomous driving. Autonomic nerve control device 100 is communicatively connected to autonomous driving system 11 for controlling the autonomous driving of moving body 10, for example.

Autonomous driving system 11 is a system including map information of the surroundings of moving body 10, a GPS (Global Positioning System) receiver for identifying the location of moving body 10, a control device, program, and the like for controlling the engine, steering, and so on of moving body 10, and the like, for moving body 10 to drive autonomously.

For example, obtainer 110 obtains destination information indicating a destination of moving body 10. Here, when control for activating the user's parasympathetic nerves is carried out, controller 130 calculates a route to the destination that is not a shortest route based on the destination information obtained by obtainer 110, and causes presenting device 220 to present the calculation result.

Note that when, for example, obtainer 110 has obtained information of the travel route of moving body 10, position information of the destination, and the like from autonomous driving system 11 while moving body 10 is driving autonomously, controller 130 may cause autonomous driving system 11 to change the position of the destination based on the user's physiological quantity and the position information of the destination obtained by obtainer 110. Additionally, controller 130 may cause autonomous driving system 11 to change the travel route based on the user's physiological quantity and the information of the travel route of moving body 10 obtained by obtainer 110, for example.

Processing Sequences

Sequences of processing by autonomic nerve control device 100 according to the embodiment will be described in detail next with reference to FIG. 3 to FIG. 8.

Figure 3:
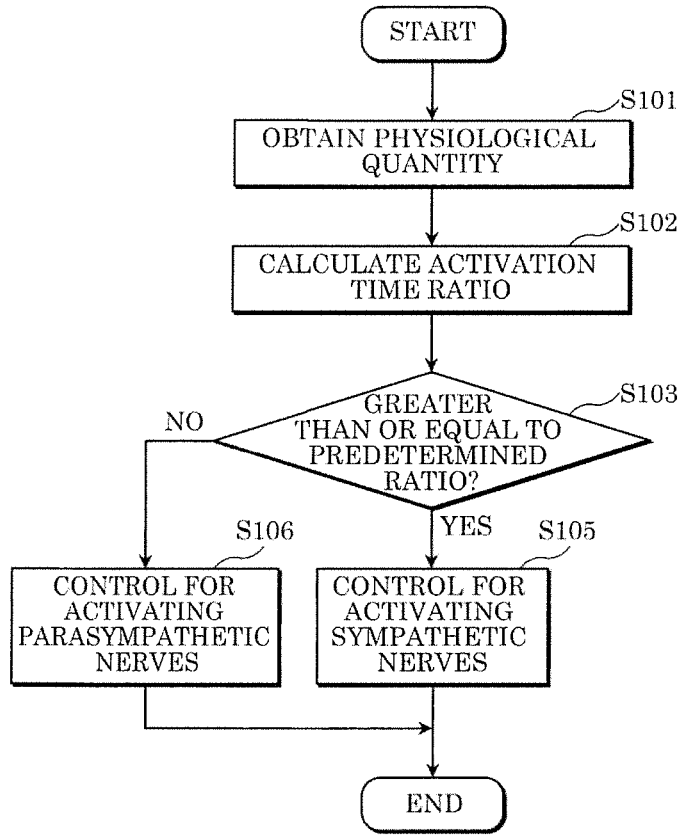
FIG. 3 is a flowchart illustrating a processing sequence through which the autonomic nerve control device controls a user's autonomic nerves, according to the embodiment.

FIG. 3 is a flowchart illustrating a processing sequence through which autonomic nerve control device 100 controls the user's autonomic nerves, according to the embodiment.

First, obtainer 110 obtains the user's physiological quantity before the user occupies moving body 10 (step S101). The user goes about his or her activities while wearing detection device 230, for example. Detection device 230 continuously detects the user's physiological quantity throughout the day, e.g., during work on the day when the user's autonomic nerves are to be controlled by controller 130, and sends the user's physiological quantity that has been detected to obtainer 110. The physiological quantity may be detected successively by detection device 230, or may be detected only a predetermined number of times.

Next, calculator 120 calculates the activation time ratio based on the user's physiological quantity obtained by obtainer 110 (step S102).

Next, controller 130 controls the user's autonomic nerves based on the activation time ratio calculated by calculator 120. Specifically, first, controller 130 determines whether or not the activation time ratio calculated by calculator 120 is greater than or equal to a predetermined ratio (step S103).

When it is determined that the activation time ratio calculated by calculator 120 is greater than or equal to the predetermined ratio (Yes in step S103), controller 130 controls output device 210 so as to activate the user's sympathetic nerves (step S105).

On the other hand, when it is determined that the activation time ratio calculated by calculator 120 is less than the predetermined ratio (No in step S103), controller 130 controls output device 210 so as to activate the user's parasympathetic nerves (step S106). For example, when breathing control device 213, which is an expanding/contracting device, is controlled to activate the user's parasympathetic nerves in step S106, controller 130 causes the expanding/contracting device, which is disposed in the backrest of a seat, to expand and contract regularly at a predetermined cycle, e.g., a cycle longer than around three seconds, or in other words, causes the seat to vibrate. Through this, controller 130 activates the user's parasympathetic nerves. Additionally, for example, when breathing control device 213, which is an expanding/contracting device, is controlled to activate the user's sympathetic nerves in step S105, controller 130 causes the expanding/contracting device, which is disposed in the backrest of the seat, to expand and contract regularly at a predetermined cycle, e.g., a cycle shorter than around three seconds, or in other words, causes the seat to vibrate. Through this, controller 130 activates the user's sympathetic nerves. The predetermined cycle is of course not limited to three seconds, and may be less than three seconds, or longer than three seconds.

The timing at which controller 130 executes step S105 and step S106 may be any timing while the user occupies moving body 10, and is not particularly limited. For example, controller 130 may execute step S105 or step S106 at the timing at which obtainer 110 has obtained the occupancy information, or may execute step S105 or step S106 at the timing at which driving is started, e.g., the timing at which obtainer 110 has obtained information from autonomous driving system 11 indicating that moving body 10 has moved.

Additionally, the amount of time for which controller 130 executes step S105 and step S106 is not particularly limited. For example, controller 130 may control the user's autonomic nerves by driving output device 210 for a predetermined amount of time. Additionally, controller 130 may determine the amount of time to drive output device 210 based on the activation time ratio calculated by calculator 120.

Additionally, the timing at which calculator 120 calculates the activation time ratio indicated in step S102 may be any timing before step S103 is executed, and is not particularly limited. For example, calculator 120 may execute step S102 at the timing at which obtainer 110 has obtained the occupancy information, or may execute step S102 at a predetermined time, or may execute step S102 every predetermined interval of time and update the user's activation time ratio with each execution.

Additionally, controller 130 may control presenting device 220 to present the user's physiological quantity obtained by obtainer 110 and the details of the control being executed to control the user's autonomic nerves after step S103, and specifically after step S105 or step S106.

Figure 4:
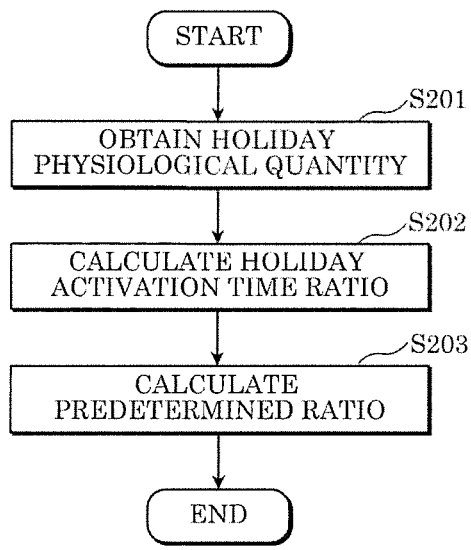
FIG. 4 is a flowchart illustrating a processing sequence through which the autonomic nerve control device calculates a holiday activation time ratio of the user's autonomic nerves, according to the embodiment.

FIG. 4 is a flowchart illustrating a processing sequence through which autonomic nerve control device 100 calculates a holiday activation time ratio of the user's autonomic nerves, according to the embodiment. In other words, FIG. 4 is a flowchart illustrating a processing sequence through which calculator 120 calculates the predetermined ratio.

First, obtainer 110 obtains the user's holiday physiological quantity before the user occupies moving body 10 (step S201). Note that holiday refers to a day on which the user is not working or a time period for which the user is not working, for example; it is sufficient for the holiday physiological quantity to be detected between when the user wakes up and when the user goes to sleep, and the holiday physiological quantity may be detected successively, or only a predetermined number of times, by detection device 230.

Next, calculator 120 calculates the user's holiday activation time ratio based on the user's physiological quantity obtained by obtainer 110 (step S202).

Next, calculator 120 calculates the predetermined ratio based on the user's holiday activation time ratio calculated in step S202 (step S203). In step S203, calculator 120 may calculate the predetermined ratio by adjusting the holiday activation time ratio based on predetermined attribute information indicating the user's gender, physique, and so on, for example.

Additionally, for example, controller 130 may select output device 210 for controlling the user's autonomic nerves, or determine the control details, based on information of music the user listens to while on holiday or a holiday breathing cycle. The information of music the user listens to while on holiday or the holiday breathing cycle may be obtained by, for example, the user inputting that information into input device 240.

Figure 5:
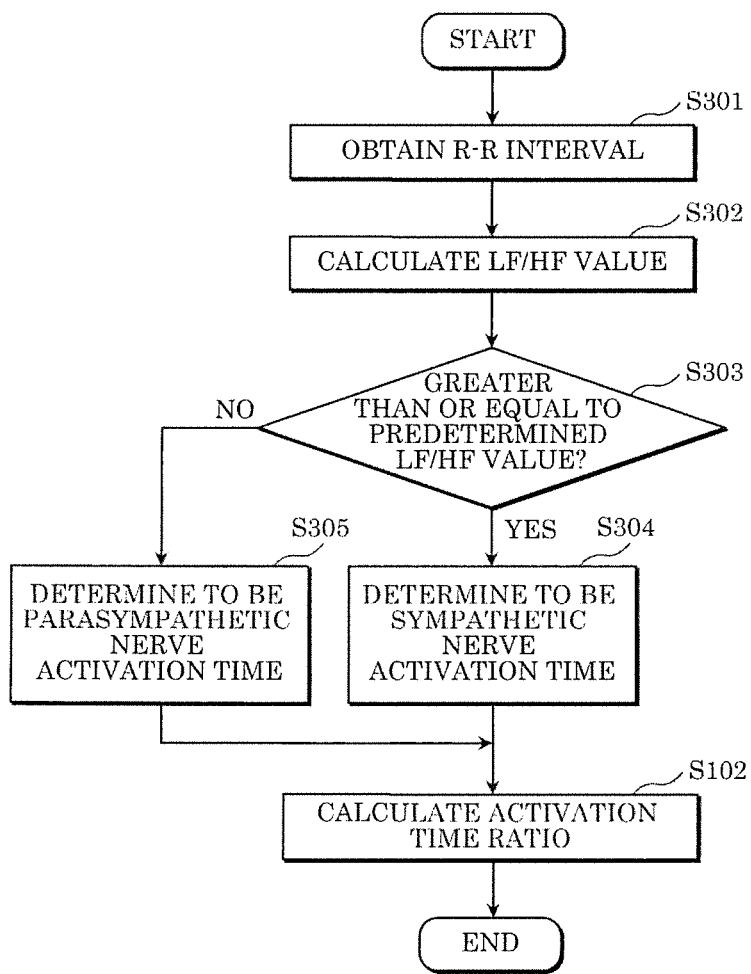
FIG. 5 is a flowchart illustrating a first example of a processing sequence through which the autonomic nerve control device calculates an activation time ratio of the user's autonomic nerves, according to the embodiment.

FIG. 5 is a flowchart illustrating a first example of a processing sequence through which autonomic nerve control device 100 calculates the activation time ratio of the user's autonomic nerves, according to the embodiment. In other words, FIG. 5 is a flowchart illustrating a sequence of processing carried out by autonomic nerve control device 100 when detection device 230 is electrocardiograph 231, or to rephrase, when the R-R interval is used as the user's physiological quantity.

First, obtainer 110 obtains the user's R-R interval, as the user's physiological quantity, before the user occupies moving body 10 (step S301).

Next, calculator 120 calculates the LF/HF value based on the user's R-R interval obtained by obtainer 110 (step S302).

Next, controller 130 determines whether or not the LF/HF value calculated by calculator 120 is greater than or equal to a predetermined LF/HF value (step S303). The predetermined LF/HF value may be determined as desired, or, like the flowchart illustrated in FIG. 4, the predetermined LF/HF value may be determined based on the user's holiday LF/HF value.

When it is determined that the LF/HF value calculated in step S302 is greater than or equal to the predetermined LF/HF value (Yes in step S303), calculator 120 determines that it is the user's sympathetic nerve activation time (step S304). In other words, in step S304, calculator 120 determines that the user's sympathetic nerves are being activated when it has been determined that the LF/HF value calculated in step S302 is greater than or equal to the predetermined LF/HF value.

On the other hand, when it is determined that the LF/HF value calculated in step S302 is less than the predetermined LF/HF value (No in step S303), calculator 120 determines that it is the user's parasympathetic nerve activation time (step S305). In other words, in step S305, calculator 120 determines that the user's parasympathetic nerves are being activated when it has been determined that the LF/HF value calculated in step S302 is less than the predetermined LF/HF value.

For example, calculator 120 executes step S303 and determines whether the user's sympathetic nerves are being activated or the user's parasympathetic nerves are being activated each time obtainer 110 obtains the R-R interval, and measures the time for which the sympathetic nerves are being activated and the time for which the parasympathetic nerves are being activated.

Next, calculator 120 calculates the user's activation time ratio from the measured time for which the sympathetic nerves are being activated and the measured time for which the parasympathetic nerves are being activated (step S102). After step S102, autonomic nerve control device 100 executes the processes of steps S103 and on, illustrated in FIG. 3.

Figure 6:
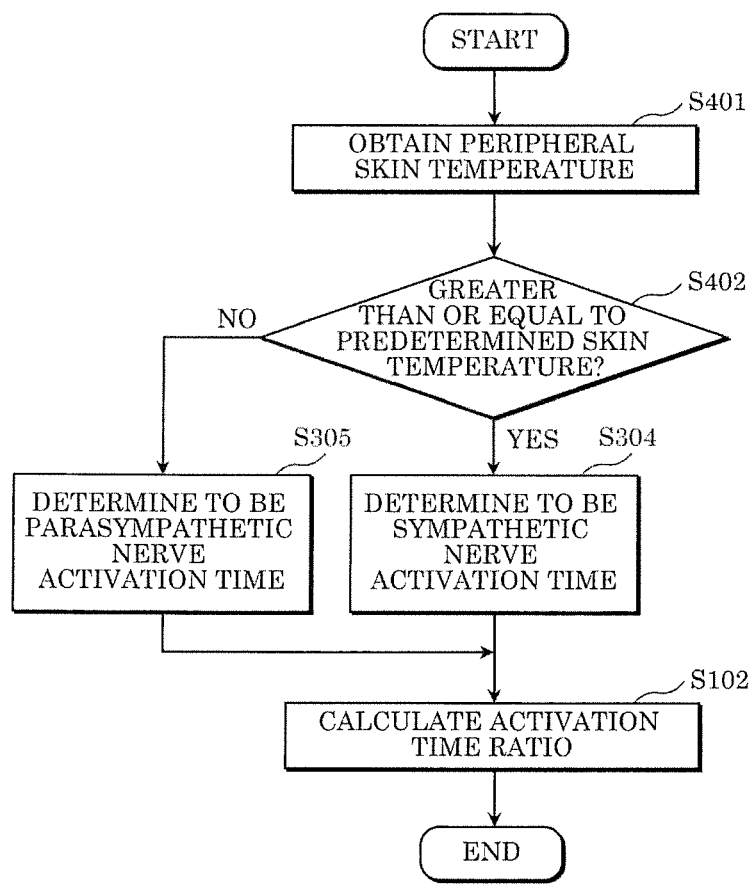
FIG. 6 is a flowchart illustrating a second example of a processing sequence through which the autonomic nerve control device calculates an activation time ratio of the user's autonomic nerves, according to the embodiment.

FIG. 6 is a flowchart illustrating a second example of a processing sequence through which autonomic nerve control device 100 calculates the activation time ratio of the user's autonomic nerves, according to the embodiment. In other words, FIG. 6 is a flowchart illustrating a sequence of processing carried out by autonomic nerve control device 100 when detection device 230 is thermometer 232, or to rephrase, when the peripheral skin temperature is used as the user's physiological quantity.

First, obtainer 110 obtains the user's peripheral skin temperature, as the user's physiological quantity, before the user occupies moving body 10 (step S401).

Next, controller 130 determines whether or not the skin temperature obtained by obtainer 110 is greater than or equal to a predetermined skin temperature (step S402). The predetermined skin temperature may be determined as desired, or, like the flowchart illustrated in FIG. 4, the predetermined skin temperature may be determined based on the user's holiday skin temperature.

When it is determined that the skin temperature obtained by obtainer 110 in step S401 is greater than or equal to the predetermined skin temperature (Yes in step S402), calculator 120 determines that it is the user's parasympathetic nerve activation time (step S304). In other words, in step S304, calculator 120 determines that the user's parasympathetic nerves are being activated when it has been determined that the skin temperature obtained by obtainer 110 in step S401 is greater than or equal to the predetermined skin temperature.

On the other hand, when it is determined that the skin temperature obtained by obtainer 110 in step S401 is less than the predetermined skin temperature (No in step S402), calculator 120 determines that it is the user's sympathetic nerve activation time (step S305). In other words, in step S305, calculator 120 determines that the user's sympathetic nerves are being activated when it has been determined that the skin temperature obtained by obtainer 110 in step S401 is less than the predetermined skin temperature.

For example, calculator 120 executes step S402 and determines whether the user's sympathetic nerves are being activated or the user's parasympathetic nerves are being activated each time obtainer 110 obtains the user's skin temperature, and measures the time for which the sympathetic nerves are being activated and the time for which the parasympathetic nerves are being activated.

Next, calculator 120 calculates the user's activation time ratio from the measured time for which the sympathetic nerves are being activated and the measured time for which the parasympathetic nerves are being activated (step S102). After step S102, autonomic nerve control device 100 executes the processes of steps S103 and on, illustrated in FIG. 3.

Figure 7:
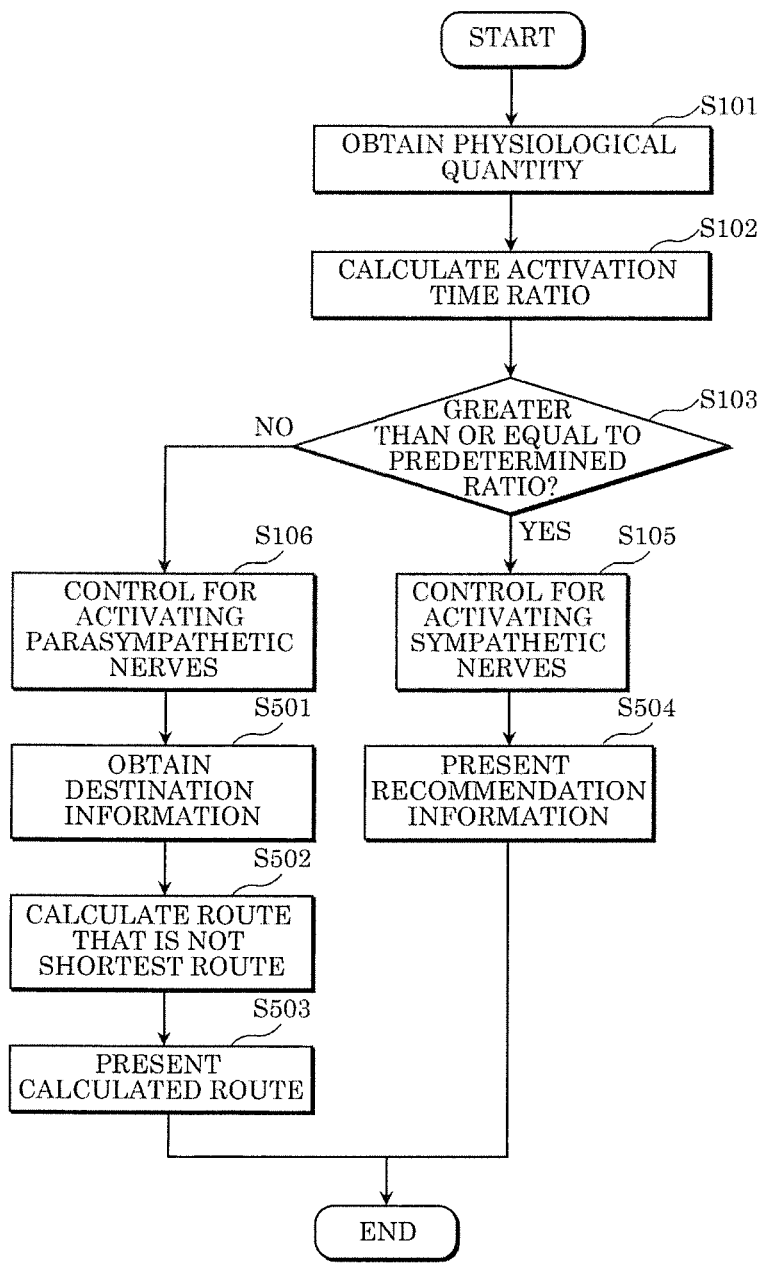
FIG. 7 is a flowchart illustrating a processing sequence through which the autonomic nerve control device presents a travel route of a moving body, according to the embodiment.

FIG. 7 is a flowchart illustrating a processing sequence through which autonomic nerve control device 100 presents a travel route of moving body 10, according to the embodiment. Note that the processes of step S101 to step S106 illustrated in FIG. 7 are the same as the processes of step S101 to step S106 illustrated in FIG. 3, and will therefore not be described.

After step S106, obtainer 110 obtains the destination information indicating the destination of moving body 10 (step S501). In step S501, obtainer 110 obtains the destination information and map information from autonomous driving system 11, which includes a car navigation system, or from input device 240, for example.

Next, controller 130 calculates a route to the destination that is not the shortest route based on the destination information obtained by obtainer 110 (step S502). In step S502, controller 130 calculates the route to the destination that is not the shortest route based on the map information obtained by obtainer 110, for example. The length of the route, road sequence, and the like calculated by controller 130 may be determined based on the user's activation time ratio, for example.

Next, controller 130 causes presenting device 220 to present the calculation result from step S502 (step S503).

Note that the timing at which obtainer 110 obtains the destination information of moving body 10 in step S501 may be before step S106.

Additionally, after step S105, controller 130 causes presenting device 220 to present the recommendation information recommending that the user walk (step S504). The recommendation information may be any information recommending that the user walk, and may be a voice, text, or the like saying "your sympathetic nerves have been activated for a long time, so it is recommended that you walk", for example.

Note that controller 130 may cause the user's physiological quantity, obtained by obtainer 110, to be stored in storage 140, for example. Additionally, calculator 120 may start calculating the activation time ratio when obtainer 110 has obtained the occupancy information.

Figure 8:
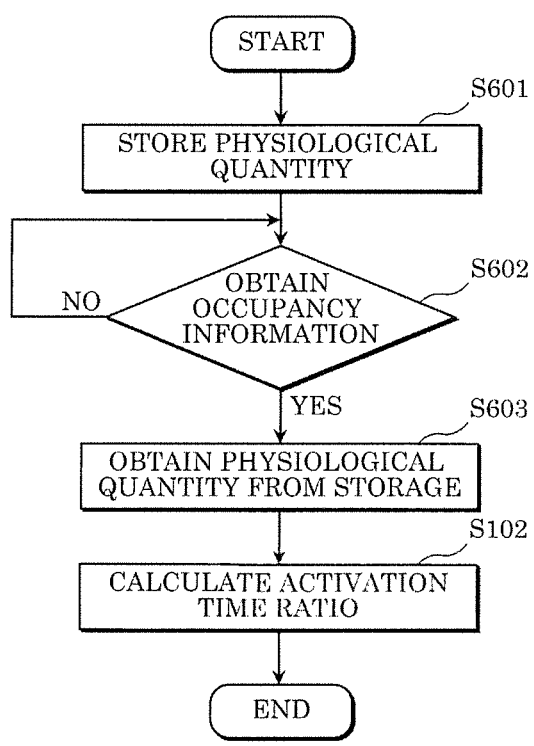
FIG. 8 is a flowchart illustrating a variation on the processing sequence through which the autonomic nerve control device controls a user's autonomic nerves, according to the embodiment.

FIG. 8 is a flowchart illustrating a variation on a processing sequence through which autonomic nerve control device 100 controls the user's autonomic nerves, according to the embodiment.

First, obtainer 110 obtains the user's physiological quantity before the user occupies moving body 10. Here, for example, controller 130 causes the user's physiological quantity obtained by obtainer 110, and time information obtained by obtainer 110, to be stored in storage 140 in association with each other (step S601).

Next, controller 130 determines whether or not obtainer 110 has obtained the occupancy information (step S602). In step S602, controller 130 determines whether or not obtainer 110 has obtained the occupancy information from a human sensor (not shown) provided in moving body 10, i.e., information indicating that the user has been detected within moving body 10, for example.

When it is determined that obtainer 110 has not obtained the occupancy information (No in step S602), controller 130 repeats the process of step S602 until obtainer 110 obtains the occupancy information.

On the other hand, when it is determined that controller 130 has obtained the occupancy information (Yes in step S602), obtainer 110 obtains the user's physiological quantity and the time information associated with the physiological quantity, stored in storage 140 (step S603). In other words, in step S603, when it is determined that obtainer 110 has obtained the occupancy information, controller 130 causes obtainer 110 to obtain the user's physiological quantity and the time information associated with the physiological quantity, which is stored in storage 140.

Next, calculator 120 calculates the sympathetic nerve and parasympathetic nerve activation times from the user's physiological quantity and the time information associated with the physiological quantity obtained from storage 140 by obtainer 110, and calculates the user's activation time ratio from the calculated time for which the sympathetic nerves are being activated and the calculated time for which the parasympathetic nerves are being activated (step S102). After step S102, autonomic nerve control device 100 executes the processes of steps S103 and on, illustrated in FIG. 3.

Effects, etc.

As described thus far, autonomic nerve control device 100 according to one aspect of the present disclosure includes: obtainer 110 that obtains a physiological quantity of a user before the user occupies moving body 10; and controller 130 that controls autonomic nerves of the user occupying moving body 10 based on the physiological quantity of the user obtained by obtainer 110.

Through this, the user's physiological quantity is obtained before the user occupies moving body 10, and thus the user's physiological quantity is obtained in a state where the physiological quantity is not being affected by vibrations or the like caused by movement in moving body 10. Additionally, the autonomic nerves of the user occupying moving body 10 are controlled based on the user's physiological quantity that has been obtained by obtainer 110, and thus when a given user among a plurality of users occupies moving body 10, favorable autonomic nerve control is executed for the user occupying moving body 10. As such, the autonomic nerves of the user occupying moving body 10 can be controlled appropriately.

Additionally, for example, autonomic nerve control device 100 further includes calculator 120 that calculates an activation time ratio, expressing a ratio of an activation time of parasympathetic nerves of the user to an activation time of sympathetic nerves of the user, from the physiological quantity of the user obtained by obtainer 110. Controller 130 carries out control for activating the sympathetic nerves of the user when the activation time ratio calculated by calculator 120 is greater than or equal to a predetermined ratio, and carries out control for activating the parasympathetic nerves of the user when the activation time ratio calculated by calculator 120 is less than the predetermined ratio.

Through this, the sympathetic nerves or parasympathetic nerves of the user occupying moving body 10 are controlled using the activation time ratio between the sympathetic nerves and the parasympathetic nerves of the user before the user occupies moving body 10. As such, the sympathetic nerves or the parasympathetic nerves of the autonomic nerves of the user occupying moving body 10 can be controlled more appropriately.

Additionally, for example, obtainer 110 obtains a holiday physiological quantity of the user. Calculator 120 calculates a holiday activation time ratio of the user from the holiday physiological quantity of the user obtained by obtainer 110, and calculates the predetermined ratio based on the calculated holiday activation time ratio of the user.

Through this, the activation time ratio during which the user's autonomic nerves are most stable, i.e., the activation time ratio of the autonomic nerves while on a holiday considered appropriate by the user, serves as a reference for the determination in the control carried out by controller 130. As such, the user occupying moving body 10 can be controlled to an autonomic nerve state that is more favorable for that user.

Additionally, for example, obtainer 110 obtains an R-R interval, calculated from a heartbeat waveform of the user, as the physiological quantity of the user. In this case, calculator 120 calculates an LF/HF value from the R-R interval obtained by obtainer 110; and calculates the activation time ratio by determining a time for which the calculated LF/HF value is greater than or equal to a predetermined LF/HF value to be an activation time of the sympathetic nerves, and determining a time for which the calculated LF/HF value is less than the predetermined LF/HF value to be an activation time of the parasympathetic nerves.

Through this, the activation time ratio can be calculated easily by calculator 120, without using complex information, simply by detecting the user's electrocardiographic waveform as the user's physiological quantity. Thus according to autonomic nerve control device 100, the user's autonomic nerves can be controlled appropriately using a simpler configuration.

Additionally, for example, obtainer 110 obtains a peripheral skin temperature of the user as the physiological quantity of the user. In this case, calculator 120 calculates the activation time ratio by determining a time for which the peripheral skin temperature obtained by obtainer 110 is less than a predetermined skin temperature to be an activation time of the sympathetic nerves, and determining a time for which the peripheral skin temperature is greater than or equal to the predetermined skin temperature to be an activation time of the parasympathetic nerves.

Through this, the activation time ratio can be calculated easily by calculator 120, without using complex information, simply by detecting the peripheral skin temperature at a fingertip, the tip of the nose, or the like of the user as the user's physiological quantity. Thus according to autonomic nerve control device 100, the user's autonomic nerves can be controlled appropriately using a simpler configuration.

Additionally, for example, controller 130 controls the autonomic nerves of the user by controlling breathing control device 213, which controls breathing of the user.

Through this, for example, the depth, rhythm, and the like of the user's breathing can be controlled by controlling a device commonly provided in moving body 10, such as an audio device or the like, to output audio guidance for communicating a breathing rhythm. According to such a configuration, the user's autonomic nerves can be controlled appropriately using a simpler configuration. Additionally, the depth, rhythm, and so on of the user's breathing can be controlled by controlling an expanding/contracting device that is disposed in a seat of moving body 10 and that is capable of expanding and contracting, for example. According to such a configuration, even when the user is using the audio device to listen to music or the like, the user's breathing can be controlled without using the audio device.

Additionally, for example, controller 130 controls the autonomic nerves of the user by controlling at least one of audio device 212 and air conditioning device 211.

Through this, the user's autonomic nerves are controlled simply by controlling a device commonly provided in moving body 10, such as audio device 212, air conditioning device 211, or the like. Thus according to autonomic nerve control device 100, the user's autonomic nerves can be controlled appropriately using a simpler configuration.

Additionally, for example, controller 130 further causes presenting device 220 to present the physiological quantity of the user and details of control being executed for controlling the autonomic nerves of the user.

Through this, the user can correctly understand his or her own biological state and the details of the control. Thus even when, for example, a device in moving body 10 has automatically begun operating to control the user's autonomic nerves, the user's autonomic nerves can be controlled appropriately without the user mistakenly stopping the device in moving body 10.

Additionally, for example, obtainer 110 further obtains destination information indicating a destination of moving body 10. When control for activating the parasympathetic nerves of the user is carried out, controller 130 calculates a route to the destination that is not a shortest route based on the destination information obtained by obtainer 110, and causes presenting device 220 to present a result of the calculation.

Through this, the user can be prompted to extend the time for which he or she occupies moving body 10. This makes it easier to activate the user's parasympathetic nerves within moving body 10. In other words, the user can become more relaxed in moving body 10.

Additionally, for example, when control is carried out for activating the sympathetic nerves of the user, controller 130 causes presenting device 220 to present recommendation information recommending that the user walk.

Through this, the activation of the sympathetic nerves can be prompted by having the user walk to his or her destination. This makes it possible to appropriately activate the user's sympathetic nerves after the user has exited moving body 10.

Additionally, for example, autonomic nerve control device 100 further includes storage 140, which stores the physiological quantity of the user. When occupancy information indicating that the user has entered moving body 10 is obtained, obtainer 110 obtains the physiological quantity of the user from storage 140.

Through this, the control of the user's autonomic nerves can be started automatically at the timing at which the user occupies moving body 10. As such, the control of the user's autonomic nerves can be started at an appropriate timing when the user is occupying moving body 10.

Additionally, autonomic nerve control system 200 according to one aspect of the present disclosure includes: autonomic nerve control device 100; detection device 230, which is disposed outside moving body 10 and which detects the physiological quantity of the user; and output device 210, which is disposed in moving body 10 and which is driven by controller 130 to control the autonomic nerves of the user occupying moving body 10.

Through this, the same effects as those of autonomic nerve control device 100 can be achieved.

Additionally, an autonomic nerve control method according to one aspect of the present disclosure is an autonomic nerve control method executed by autonomic nerve control device 100, and includes: obtaining a physiological quantity of a user before the user occupies moving body 10; and controlling autonomic nerves of the user occupying moving body 10 based on the physiological quantity of the user obtained in the obtaining step.

Through this, the user's physiological quantity is obtained before the user occupies moving body 10, and thus the user's physiological quantity can be obtained in a state where the physiological quantity is not being affected by vibrations or the like caused by movement in moving body 10. Additionally, the autonomic nerves of the user occupying moving body 10 are controlled based on the user's physiological quantity that has been obtained, and thus when a given user among a plurality of users occupies moving body 10, favorable autonomic nerve control is executed for the user occupying moving body 10. Thus with the autonomic nerve control method according to one aspect of the present disclosure, the autonomic nerves of a user occupying moving body 10 can be controlled appropriately.

OTHER EMBODIMENTS

The foregoing has described an autonomic nerve control device, an autonomic nerve control system, and an autonomic nerve control method according to the present disclosure based on embodiments and variations, but the present disclosure is not limited to the foregoing embodiments. For example, embodiments achieved by one skilled in the art making various conceivable variations on the embodiments, embodiments achieved by combining constituent elements and functions from the embodiments as desired within a scope which does not depart from the spirit of the present disclosure, and the like are also included in the present disclosure.

For example, constituent elements such as processors included in autonomic nerve control device 100, e.g., calculator 120, controller 130, and the like, may be constituted by one or more electronic circuits. The one or more electronic circuits may be generic circuits, or may be dedicated circuits. The one or more electronic circuits may include semiconductor devices, ICs (Integrated Circuit), LSI (Large Scale Integration) circuits, or the like, for example. The ICs or LSI circuits may be integrated on a single chip, or may be integrated on a plurality of chips. Although the terms IC and LSI are used here, the terminology differs depending on the degree of integration, and these may therefore be called system LSI, VLSI (Very Large Scale Integration), or ULSI (Ultra Large Scale Integration). An FPGA (Field Programmable Gate Array), which is programmed after an LSI circuit is manufactured, can be used for the same purpose.

The general or specific forms of the present disclosure may be implemented as systems, devices, methods, integrated circuits, or computer programs. These forms may instead be implemented by a computer-readable non-transitory recording medium, such as an optical disk, an HDD, semiconductor memory, or the like, in which the computer program is stored. These forms may also be implemented by any desired combination of systems, devices, methods, integrated circuits, computer programs, and recording media.

Additionally, while the foregoing embodiment described detection device 230 and obtainer 110 as being capable of communication, the method of communication between detection device 230 and obtainer 110 is not particularly limited. The communication may be carried out based on a predetermined wireless communication standard such as Bluetooth (registered trademark), Wi-Fi (registered trademark), ZigBee (registered trademark), or the like, for example. Additionally, when autonomic nerve control device 100 is disposed outside moving body 10, detection device 230 and obtainer 110 may communicate over a wire. In this case, detection device 230 and obtainer 110 may include communication adapters or the like for connecting cables for communicating with each other over the wire. Like detection device 230, external devices such as presenting device 220, input device 240, and the like may be communicatively connected to obtainer 110 wirelessly, or may be communicatively connected over a wire.

Additionally, for example, the user's physiological quantity detected by detection device 230 may be processed using what is known as cloud computing. For example, the user's physiological quantity detected by detection device 230 may be stored in a server device or the like communicatively connected to detection device 230. In this case, obtainer 110 may be communicatively connected to the server device, and may obtain the user's physiological quantity from that server device.

Of course, the user's physiological quantity may be detected within moving body 10 as well. In other words, autonomic nerve control system 200 may further include, within moving body 10, a detection device that detects the user's physiological quantity. Autonomic nerve control device 100 may obtain the user's physiological quantity within moving body 10 and cause presenting device 220 to present the user's physiological quantity which has been obtained, for example. By doing so, the user can confirm the effects that the control by autonomic nerve control device 100 have had on the user's autonomic nerves within moving body 10. Of course, the user may control autonomic nerve control device 100 in light of that result. For example, by confirming the user's physiological quantity within moving body 10, presented by presenting device 220, and then operating input device 240, the user inputs instructions that control a desired output device 210 according to desired control details. Autonomic nerve control device 100 may change the details of the control of output device 210 based on the instructions from the user input to input device 240, for example. Additionally, for example, autonomic nerve control device 100 may change the details of the control of output device 210 based on the user's physiological quantity which has been obtained within moving body 10.

Additionally, aside from the user's physiological quantity, environment information indicating the environment within moving body 10 may be obtained as the information obtained by obtainer 110, for example. The environment information is information including a noise level, a temperature, and the like within moving body 10, for example. For example, the sympathetic nerves activate when there is a high level of noise within moving body 10, and the sympathetic nerves also activate when it is hot, cold, or the like. Additionally, obtainer 110 may obtain warm-cold sense information to obtain the user's sense of feeling warm, cold, or the like, for example. The warm-cold sense is information indicating the user's sense of feeling warm, cold, or the like, and is information indicating a thermal image of the driver, for example. Controller 130 may control the user's autonomic nerves by controlling air conditioning device 211 based on the temperature within moving body 10 and the user's thermal image so as to control the cabin temperature within moving body 10. Accordingly, controller 130 may control the user's autonomic nerves based on the user's physiological quantity and the environment information. In this case, autonomic nerve control system 200 may further include a sensor for obtaining the environment information.

INDUSTRIAL APPLICABILITY

The present disclosure can be used in a system that appropriately controls the autonomic nerves of a user occupying a moving body in accordance with that user, and is used in, for example, a device or the like that controls a user's autonomic nerves by controlling an audio device, an air conditioning device, and the like provided in a vehicle.

The invention claimed is:

1. An autonomic nerve control device, comprising:
    an obtainer that obtains a peripheral skin temperature of a user as a physiological quantity of the user before the user occupies a moving body;
    a calculator that calculates an activation time ratio, expressing a ratio of an activation time of parasympathetic nerves of the user to an activation time of sympathetic nerves of the user, by determining a time for which the peripheral skin temperature obtained by the obtainer is less than a predetermined skin temperature to be the activation time of the sympathetic nerves, and determining a time for which the peripheral skin temperature obtained by the obtainer is greater than or equal to the predetermined skin temperature to be the activation time of the parasympathetic nerves; and
    a controller that controls autonomic nerves of the user occupying the moving body by carrying out control for activating the sympathetic nerves of the user when the activation time ratio calculated by the calculator is greater than or equal to a predetermined ratio, and carrying out control for activating the parasympathetic nerves of the user when the activation time ratio calculated by the calculator is less than the predetermined ratio.

2. The autonomic nerve control device according to claim 1,
    wherein the obtainer obtains a holiday physiological quantity of the user, and
    the calculator calculates a holiday activation time ratio of the user from the holiday physiological quantity of the user obtained by the obtainer, and calculates the predetermined ratio based on the calculated holiday activation time ratio of the user.

3. The autonomic nerve control device according to claim 1,
    wherein the controller controls the autonomic nerves of the user by controlling a breathing control device that controls breathing of the user.

4. The autonomic nerve control device according to claim 1,
wherein the controller controls the autonomic nerves of the user by controlling at least one of an audio device and an air conditioning device.

5. The autonomic nerve control device according to claim 1,
wherein the controller further causes a presenting device to present the physiological quantity of the user and details of control being executed for controlling the autonomic nerves of the user.

6. The autonomic nerve control device according to claim 1,
wherein the obtainer further obtains destination information indicating a destination of the moving body; and
when control for activating the parasympathetic nerves of the user is carried out, the controller calculates a route to the destination that is not a shortest route based on the destination information, and causes a presenting device to present a result of the calculation.

7. The autonomic nerve control device according to claim 1,
wherein when control is carried out for activating the sympathetic nerves of the user, the controller causes a presenting device to present recommendation information recommending that the user walk.

8. The autonomic nerve control device according to claim 1, further comprising:
a storage unit that stores the physiological quantity of the user,
wherein when occupancy information indicating that the user has entered the moving body is obtained, the obtainer obtains the physiological quantity of the user from the storage unit.

9. An autonomic nerve control system comprising:
the autonomic nerve control device according to claim 1;
a detecting device that is disposed outside the moving body and that detects the physiological quantity of the user; and
an output device that is disposed in the moving body and that is driven by the controller to control the autonomic nerves of the user occupying the moving body.

10. An autonomic nerve control method comprising:
obtaining a peripheral skin temperature of a user as a physiological quantity of the user before the user occupies a moving body; and
calculating an activation time ratio, expressing a ratio of an activation time of parasympathetic nerves of the user to an activation time of sympathetic nerves of the user, by determining a time for which the obtained peripheral skin temperature is less than a predetermined skin temperature to be the activation time of the sympathetic nerves, and determining a time for which the obtained peripheral skin temperature is greater than or equal to the predetermined skin temperature to be the activation time of the parasympathetic nerves; and
controlling autonomic nerves of the user occupying the moving body by carrying out control for activating the sympathetic nerves of the user when the calculated activation time ratio is greater than or equal to a predetermined ratio, and carrying out control for activating the parasympathetic nerves of the user when the calculated activation time ratio is less than the predetermined ratio.

\* \* \* \* \*